(12) United States Patent
Fauth et al.

(10) Patent No.: US 8,441,646 B2
(45) Date of Patent: May 14, 2013

(54) SENSOR DEVICE AND METHOD FOR DETECTING THE TURBIDITY OF WASH LIQUOR

(75) Inventors: Michael Fauth, Pleinfeld (DE); Reinhard Hering, Holzheim (DE); Bernd Kränzle, Demmingen (DE)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 503 days.

(21) Appl. No.: 12/667,697

(22) PCT Filed: Jun. 30, 2008

(86) PCT No.: PCT/EP2008/058392
§ 371 (c)(1),
(2), (4) Date: Jan. 11, 2010

(87) PCT Pub. No.: WO2009/007268
PCT Pub. Date: Jan. 15, 2009

(65) Prior Publication Data
US 2010/0195091 A1    Aug. 5, 2010

(30) Foreign Application Priority Data
Jul. 6, 2007    (DE) .......................... 10 2007 031 480

(51) Int. Cl.
*G01N 21/00*    (2006.01)
(52) U.S. Cl.
USPC .................. 356/442; 356/51; 8/137; 134/57 D
(58) Field of Classification Search .................. 356/300, 356/317, 423–44, 441, 442, 51; 8/137
See application file for complete search history.

(56) References Cited

U.S. PATENT DOCUMENTS

| | | | | |
|---|---|---|---|---|
| 4,257,708 A * | 3/1981 | Fukuda | ......................... | 356/435 |
| 5,373,714 A | 12/1994 | Wada | | |
| 5,589,935 A * | 12/1996 | Biard | ............................ | 356/339 |
| 5,800,628 A * | 9/1998 | Erickson et al. | ................. | 134/18 |
| 2003/0173530 A1* | 9/2003 | Schenkl | ........................ | 250/573 |
| 2004/0135089 A1 | 7/2004 | Manz et al. | | |
| 2007/0046942 A1 | 3/2007 | Ng et al. | | |
| 2009/0059218 A1* | 3/2009 | Harner et al. | ............. | 356/243.2 |

FOREIGN PATENT DOCUMENTS

| | | |
|---|---|---|
| DE | 250777 A1 | 10/1987 |
| DE | 250778 A1 | 10/1987 |
| DE | 4403418 A1 * | 8/1995 |
| DE | 10111006 A1 | 11/2002 |
| DE | 10356279 A1 | 6/2004 |
| EP | 1543764 A2 * | 6/2005 |

* cited by examiner

*Primary Examiner* — Tarifur Chowdhury
*Assistant Examiner* — Michael P Lapage
(74) *Attorney, Agent, or Firm* — James E. Howard; Andre Pallapies (57) ABSTRACT

A sensor device and method for detecting the turbidity of wash liquor. The sensor device includes an optical transmitter; an optical receiver, wherein the wash liquor to be tested flows between the transmitter and the receiver; and an electronic control and evaluation device to (a) carry out a reference measurement by means of the optical transmitter and receiver in order to determine a reference measured value; (b) carry out a turbidity measurement on the wash liquor to be measured by means of the optical transmitter and receiver in order to determine a test measured value; (c) relate the reference measured value to the test measured value; and (d) determine a characteristic value for a determined turbidity of the wash liquor therefrom and transmit the characteristic value as a measurement signal. The determination of the reference measured value and the test measured value include determining a gradient of the turbidity.

27 Claims, 6 Drawing Sheets

SENSOR DEVICE AND METHOD FOR DETECTING THE TURBIDITY OF WASH LIQUOR

BACKGROUND OF THE INVENTION

The invention relates to a sensor device for detecting the turbidity of wash liquor with an optical transmitter and an optical receiver, wherein the wash liquor to be tested flows between the transmitter and the receiver. The sensor device comprises an electronic evaluation device which is designed to use the optical transmitter and the receiver to carry out a reference measurement in order to determine a reference measured value, use the optical transmitter and the receiver to carry out a turbidity measurement on the wash liquor to be measured in order to determine a test measured value, relate the reference measured value to the test measured value, and determine a characteristic value for the determined turbidity of the wash liquor therefrom and emit said characteristic value as a measurement signal.

The invention also relates to a method for detecting the turbidity of wash liquor, in particular in a domestic dishwasher, in which the wash liquor to be tested flows between a transmitter and a receiver, wherein a reference measurement is carried out in order to determine a reference measured value, a turbidity measurement on the wash liquor to be measured is carried out in order to determine a test measured value, the reference measured value is related to the test measured value, and a characteristic value for the determined turbidity of the wash liquor is determined therefrom and said characteristic value is emitted as a measurement signal.

The use of such sensor devices, also called "turbidity sensors" for short, is advantageous when operating washing machines, dishwashers and the like. By determining the turbidity of the wash or rinse liquor it is possible with repeated wash or rinse cycles to determine when this liquor is clean enough and a rinse cycle can therefore be ended. As a result it is possible to adjust the number of wash or rinse cycles or the duration of individual subprogram steps to the actual conditions with more or less heavily contaminated laundry or items to be washed and not set the rinse cycles or sub-program steps to the highest level of contamination allowed independently of the level of contamination of the wash liquor. A turbidity sensor thus contributes to a significant reduction in the amount of wash or rinse liquor required. At the same time the addition of detergent can be matched to the actual degree of contamination measured by the turbidity sensor. This means that it is also possible to reduce cleaning substances.

Turbidity Sensors are Basically Known.

A generic sensor device for detecting the turbidity of wash liquor with an optical transmitter and an optical receiver, wherein the wash liquor to be tested flows between the transmitter and receiver, is known from DE 44 03 418 A1. The optical conditions in the measuring room are firstly determined herein by carrying out a reference measurement before the actual turbidity measurement. This means the degree of contamination of the turbidity sensor and/or the possible degree of contamination of the reference liquid is determined. This measured value defines the contamination in the measuring room and is defined as the base value. The actual measured value that then takes place (on the basis of the measurement of the contaminated liquid for testing) is related to the reference value. The resulting difference is processed further as the measured signal as the relative contamination or turbidity.

To carry out the reference and/or test measurement a gradually increasing voltage is applied to the optical sensor by a digital-to-analog converter in order to generate a gradually increasing brightness in the sensor. When a sufficiently bright signal is detected the receiver emits an electrical signal to an evaluation device which then ends generation of the voltage for the transmitter and generates the measurement signal. At the instant at which the receiver detects a signal that is sufficiently bright to penetrate turbid liquid additional voltage levels are ended for the optical transmitter by generating an electrical signal at the output of the receiver. The counter count reached in the evaluation device is "frozen" and is used as a gauge of the measured turbidity.

DE 101 11 006 A1 discloses a method for adjusting and correcting a turbidity sensor to changing conditions at the measuring site, calibration or reference values being determined as the wash program is running in order to adjust the sensor and correct the turbidity sensor in the case of turbidity measurements on the wash liquor. A plurality of calibration measurements is carried out within one wash program in this case, at instants at which it is highly probable that there is clear water at the measuring site of the turbidity sensor in each case. The most optimal reference value is used for turbidity value correction, and this is obtained by averaging a plurality of reference values that were determined in a plurality of wash program cycles.

DE 103 56 279 A1 describes a sensor switch for detecting a level of turbidity in a liquid, for example the wash liquid of a dishwasher. However, in this case it is only possible to detect certain levels of turbidity that are fixed by the configuration of the electronic evaluation device. It is not possible to determine an absolute level of turbidity.

DE 101 19 932 A1 describes a transmission sensor with first and second measured sections. A transmitter emits electromagnetic radiation in both measured sections. The first measured section is associated with a first receiver and the second measured section is associated with a second receiver. A measured value calibration is carried out in which a first calibration value that correlates with the intensity of the radiation transmitted by the first measured section and a second calibration value that correlates with the intensity of the radiation transmitted by the second measured section are determined. Normalized measured values are used when determining a turbidity value that correlates with the turbidity of the fluid. A first measured value that correlates with the intensity of the radiation transmitted by the first measured section and a second measured value that correlates with the intensity of the radiation transmitted by the second measured section are firstly determined for this purpose. A first normalized measured value is then formed by the quotient from the first measured value and first calibration value and a second normalized measured value is formed by the quotient from the second measured value and second calibration value. The turbidity value is determined using these normalized measured values. The state of the fluid during the measured value calibration is defined as the reference state, so the determined turbidity value indicates the deviation from this reference state. The purpose of this procedure is to eliminate the effects of dirt depositing on the transmitter and/or receivers. Aging phenomena in the transmitter and/or receivers are also neutralized. Power fluctuations in the transmitter and receivers used, which can occur during production, are also neutralized.

Figure 1:
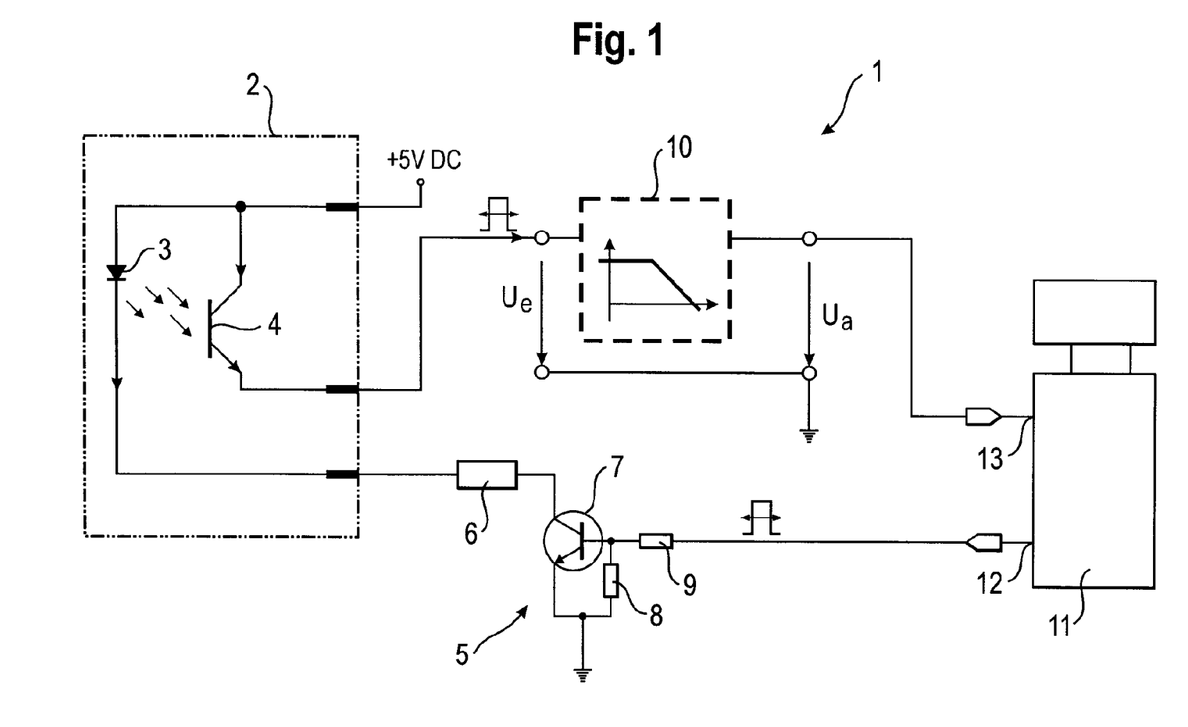
FIG. 1 shows an electrical equivalent circuit diagram of a sensor device that can be used within the scope of the invention.
Figure 2:
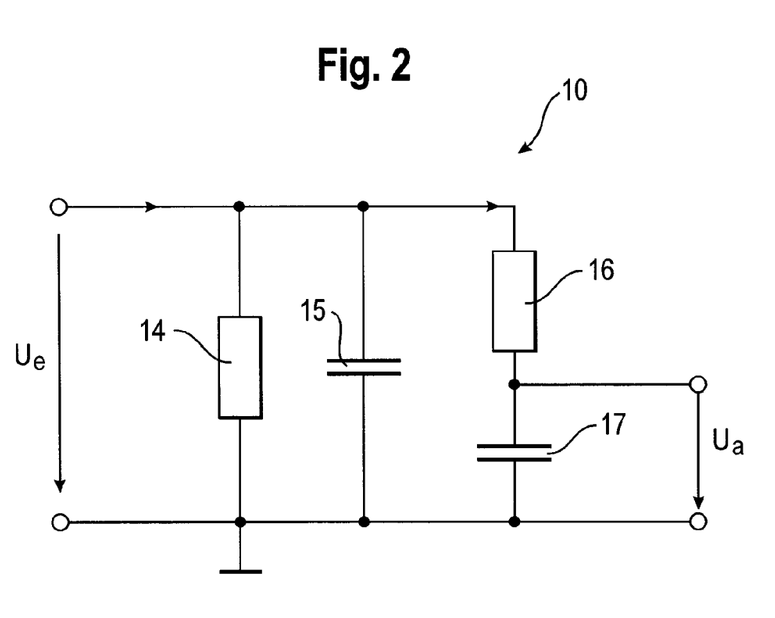
FIG. 2 shows an exemplary embodiment of an anti-aliasing filter which is used in the circuit in FIG. 1.

FIG. 1 shows a schematic diagram of an electrical equivalent circuit diagram of a sensor device 1, used, for example, in domestic dishwashers. The sensor device 1 comprises a turbidity sensor 2 which is also called an "aqua sensor". The turbidity sensor 2 comprises an optical transmitter 3, coupled to a supply voltage Vcc, and a receiver 4, in the form of a phototransistor, coupled to the optical transmitter 3. As is known, the luminous intensity emitted by the transmitter 3 depends on the current that flows through it. For this purpose a circuit 5 coupled to the transmitter 3 is provided which can be controlled via an output 12 of a control and evaluation device 11. The transmitter 3 is controlled by means of pulse-width modulation in that a transistor 7 in the circuit 5 connects the transmitter 3 to a reference potential via a resistor 6 according to its control. Depending on the pulse-duty factor set, an average current is produced through the transmitter 3, resistor 6 and conductive transistor 7 in the direction of the reference potential. The receiver 4, designed as a phototransistor, is coupled by its emitter via a circuit block 10, configured as an anti-aliasing filter, to an input 13 of the control and evaluation device 11. A pulsed current is applied to the input of the circuit block 10 due to the transmitter 3 being controlled with a pulse-width modulated signal. The pulsed photocurrent is converted into direct voltage $U_a$ by the circuit block 10. FIG. 2 shows one possible embodiment of the circuit block 10. A resistor 14 converts the current applied to the input into a voltage $U_e$. The charge-coupled accumulators 15 and 17 and the resistor 16 are used for low-pass filtering the input signal. The output voltage $U_a$, which can be supplied for further evaluation to the control and evaluation device 11 via its input 13, can be tapped at the charge-coupled accumulator 17.

Conventionally both the receiver 4 and the transmitter 3 of the sensor device 1 have different manufacturing tolerances, for which reason it is necessary to calibrate the sensor device. For this purpose the sensor device is firstly operated in defined conditions to determine a reference measured value. This conventionally takes place with clear wash liquor or in the absence of wash liquor.

Figure 3:
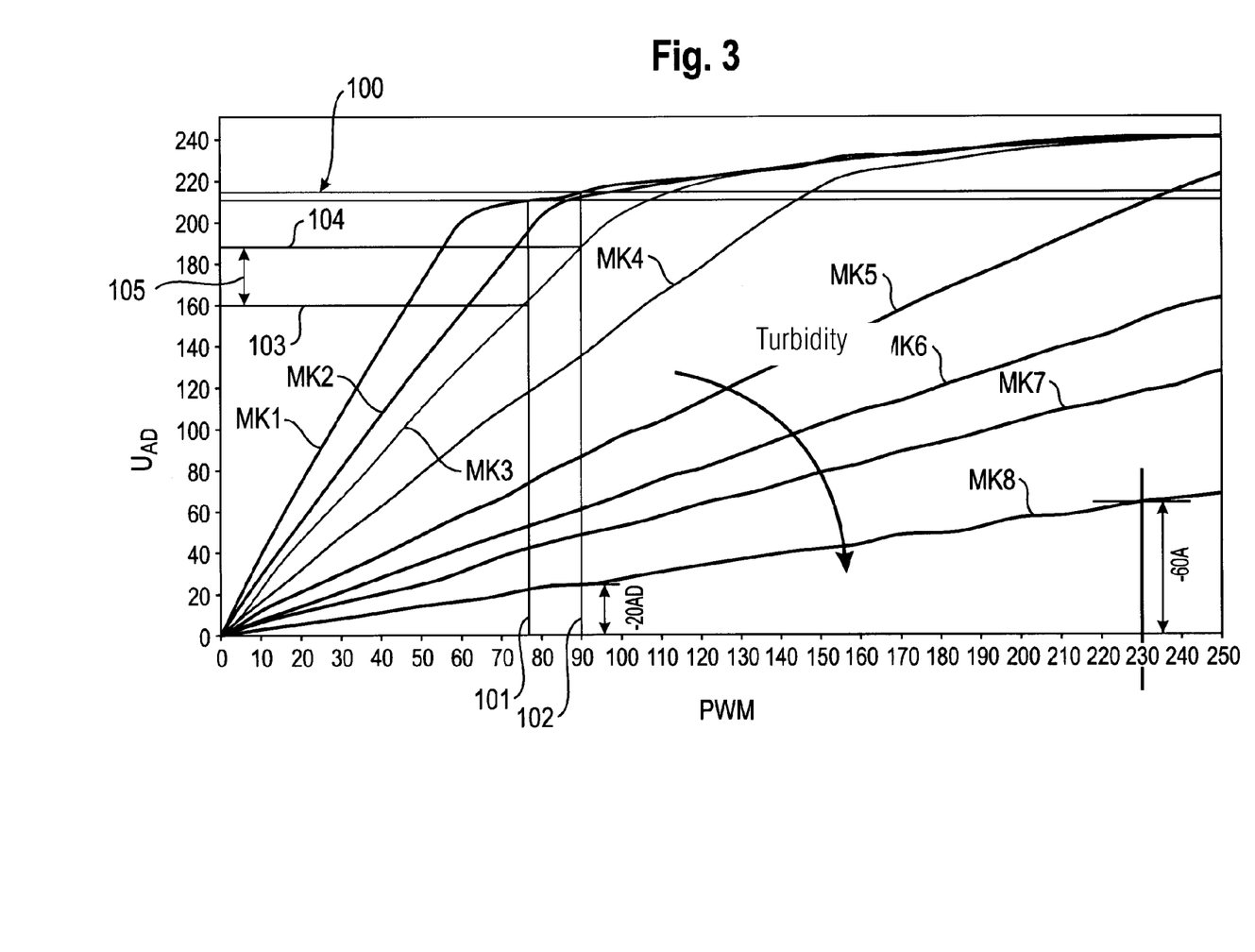
FIG. 3 shows a graph illustrating the connection between A/D converted voltage at the input of a control and evaluation device of the sensor device and pulse width in digits in the case of different turbidities.

If the sensor device 1 described in connection with FIG. 1 is operated with different pulse-duty factors, an output voltage $U_a$ that is dependent on the pulse-duty factor is produced, and this is passed to the control and evaluation device 11 for further processing. FIG. 3 shows the connection between the pulse/pause ratio PWM (pulse-duty factor) and voltage $U_{AD}$ ($=U_a$), which has already been A/D converted in the figure at hand. The figure is based on the assumption that an analog-to-digital converter with an 8-bit width is used. The pulse-duty factor is likewise shown in digital form.

To calibrate the sensor device, the sensor, starting from a pulse-duty factor 0, is operated with an increasing pulse-duty factor and, at the same time, the output voltage $U_a$ is monitored by the control and evaluation device 11. As soon as the voltage $U_a$, which matches the measure of turbidity, is within a predefined calibration window (cf. reference character 100 in FIG. 3), the calibration procedure is terminated and the pulse-duty factor present in the case of the determined voltage $U_{AD}$ ($=U_a$) is stored for the additional measuring processes. This procedure can clearly be seen in FIG. 3 in which measured curve MK1 depicts the characteristic of the voltage or turbidity as a function of the pulse-duty factor during calibration of the sensor device. As may easily be seen from the figure, measured curve MK1 has a linear region and a saturation region. Measured curve MK1 crosses the calibration window 100 in its saturation region. As may easily be seen, calibration can be terminated at a voltage between 160 and 190 digits (cf. reference characters 103 and 104). The pulse-duty factors 101, 102 associated with voltages 103, 104 are plotted accordingly.

Pulse-duty factors that differ from each other can therefore result depending on where voltage $U_a$ comes to rest within the voltage difference 105, for which reason calibration has a certain inaccuracy.

Additional measured curves MK2, MK3, MK4, MK5, MK6, MK7 and MK8 are plotted in FIG. 3, and these exhibit increasing turbidity in their linear regions. The turbidity of the measured wash liquor increases as the gradient decreases here.

Determination in the described manner of a reference value in the case of clear or no wash liquor therefore results in the sensor device being operated with a relatively low pulse-duty factor for the further measurements with contaminated wash liquor.

BRIEF SUMMARY OF THE INVENTION

It is therefore the object of the present invention to disclose a sensor device and a method for detecting the turbidity of wash liquor which produce much improved determination of the turbidity level of liquid.

This object is achieved by a sensor device with the features of claim 1 and by a method for detecting the turbidity of wash liquor with the features of claim 14. Advantageous embodiments result from the dependent claims.

Where the term 'wash liquor' is mentioned below, this should not be understood as limiting; instead this can be taken to mean any type of liquid.

An inventive sensor device for detecting the turbidity of wash liquor has an optical transmitter and an optical receiver, wherein the wash liquor to be tested flows between the transmitter and the receiver. The sensor device also comprises an electronic control and evaluation device which is designed to (a) use the optical transmitter and the receiver to carry out a reference measurement in order to determine a reference value, (b) use the optical transmitter and the receiver to carry out a turbidity measurement on the wash liquor to be measured in order to determine a test measured value, (c) relate the reference measured value to the test measured value, and (d) determine a characteristic value for the determined turbidity of the wash liquor therefrom and emit said characteristic value as a measurement signal. The sensor device is characterized in that the determination of the reference measured value and the determination of the test measured value involve determining a gradient of the turbidity.

The invention is based on the recognition that there is a linear relationship between the turbidity of a wash liquor to be measured and the gradient of the turbidity. The invention makes use of this knowledge by firstly determining the gradient of the turbidity of clear, uncontaminated wash liquor as a reference measured value. The extent of turbidity can then be inferred using a further determination of the gradient of the turbidity of "contaminated" wash liquor to be measured. In the process the invention makes it possible to easily and precisely determine an absolute value of turbidity of the wash liquor to be measured.

According to one embodiment of the inventive sensor device the illumination level emitted by the transmitter can be adjusted by the control and evaluation device using a PWM signal (pulse-width modulation), wherein, as a function of the received illumination level, the receiver can supply the evaluation device with a voltage value for determining the characteristic value characterizing the turbidity. For determining the gradient the control and evaluation device is also designed to adjust a plurality of PWM signals with different pulse-duty factors, to detect the voltage values resulting with the different pulse-duty factors in each case, and to determine the gradient of the turbidity from the plurality of detected pairs of values.

For this purpose the control and evaluation device has a microcomputer which sets the level of the current flowing through the transmitter by means of pulse-width modulation or the pulse-duty factor. The control and evaluation device also has a A/D converter with which the voltage generated by the receiver can be digitized and can be processed further by the control and evaluation device. This procedure is based on the recognition that there is also a linear relationship between the pulse-duty factor, with which the transmitter of the sensor device is controlled, and the voltage emitted by the receiver.

According to a further embodiment the control and evaluation device is designed to carry out a plurality of measurements for each of the different pulse-duty factors, in which one voltage value respectively is determined, wherein after averaging all measured voltage values the characteristic value characterizing the turbidity is determined and taken into account for further processing. The accuracy when determining the gradient may be increased further hereby. By way of example, particles located in the measured section at the instant of measuring, which would lead to an altered result in the case of a single measurement, can be compensated.

According to a further embodiment it is provided that the control and evaluation device can perform a test as to whether the characteristic value characterizing the turbidity is still in a linear working area of the sensor device. The evaluation device is designed to carry out the gradient determination if a predefined condition is met. This means the pulse-duty factor is varied within the framework of gradient determination until the condition is met. The predefined condition is preferably a predefinable voltage value. This is preferably chosen such that it lies outside of the saturation region of the working area of the sensor device but utilizes the linear working area as far as possible.

According to a further embodiment, for determining the gradient with the control and evaluation device the step size of the pulse-duty factor is incremented in the linear region, wherein the increment can be adjusted as a function of the desired measuring accuracy. The smaller the increment is selected to be, the more time is required for determining the gradient of turbidity. Conversely, the time for determining the gradient can be reduced by a larger increment. In practice an increment of 4% has proven expedient, i.e. to run through the entire pulse-duty factor from 0% to 100% a total of 25 different measurements are carried out.

To determine the gradient the total of the measured values is compared with the total of the measured pulse-duty factors. The characteristic value, which characterizes the turbidity, is calculated according to the following formula:

$$turb = \left(1 - \frac{MG}{CG}\right) * 100\%,$$

where turb is the turbidity,
MG is the measured gradient, and
CG is the calibration gradient.

Whereas the reference measured value is determined without or with clear wash liquor, according to a further embodiment it is provided that the test measured value is determined in a rinse cycle that follows the reference measurement.

The optical transmitter and the optical receiver preferably work on the basis of infrared.

The inventive sensor device can, in principle, be used to detect the turbidity of any desired liquid. Use in a dishwasher or a washing machine is especially provided, which machines are designed for domestic use in particular.

With an inventive method for detecting the turbidity of wash liquor, in particular in a domestic dishwasher, in which the wash liquor to be tested flows between a transmitter and a receiver, the following steps are provided (a) a reference measurement is carried out in order to determine a reference measured value, (b) a turbidity measurement on the wash liquor to be measured is carried out in order to determine a test measured value, (c) the reference measured value is related to the test measured value, and (d) a characteristic value for the determined turbidity of the wash liquor is determined therefrom and said characteristic value is emitted as a measurement signal. According to the invention a gradient of the turbidity is determined as a reference measured value and a test measured value.

The same advantages are connected with the inventive method as have been described above in connection with the inventive sensor device.

In one embodiment of the inventive method the illumination level emitted by the transmitter is adjusted by the control and evaluation device using a PWM signal, wherein, as a function of the received illumination level, the receiver supplies the control and evaluation device with a voltage value for determining the characteristic value characterizing the turbidity. The evaluation device adjusts a plurality of PWM signals with different pulse-duty factors for determining the gradient. It detects the voltage values resulting with the different pulse-duty factors in each case, and determines the gradient of the turbidity from the plurality of detected pairs of values.

In a further embodiment the evaluation device carries out a plurality of measurements for each of the different pulse-duty factors, in which one voltage value respectively is determined, wherein after averaging all measured voltage values the characteristic value characterizing the turbidity is determined and taken into account for further processing.

The evaluation device preferably tests whether the measured value is still in a linear working area of the sensor device. Gradient determination is carried out if the measured value meets a predefined condition. According to a further embodiment the predefined condition is a predefinable voltage value. This is chosen such that measured values are determined with different pulse-duty factors solely in the linear working area of the sensor device.

According to a further embodiment it is provided that for determining the gradient with the evaluation device the step size of the pulse-duty factor is incremented in the linear region, wherein the increment is adjusted as a function of the desired measuring accuracy.

To determine the gradient it is provided that the total of the measured values is compared with the total of the measured pulse-duty factors. The characteristic value characterizing the turbidity is calculated according to the following formula:

$$turb = \left(1 - \frac{MG}{CG}\right) * 100\%.$$

A further embodiment provides that the reference measured value is determined without wash liquor or with clear wash liquor. The test measured value is determined in a rinse cycle that follows the reference measurement.

BRIEF DESCRIPTION OF THE DRAWINGS

The invention will be described in more detail hereinafter with reference to the figures, in which.

DETAILED DESCRIPTION OF EXEMPLARY EMBODIMENTS OF THE PRESENT INVENTION

FIG. 1 shows the basic circuit diagram, already described, of the inventive sensor device 1. The turbidity sensor 2 comprises a measured section formed between the transmitter 3 and the receiver 4. The turbidity sensor 2 preferably has a forked design, so the wash liquor to be monitored can flow in the region inbetween. The transmitter 3, for example an infrared LED, emits light, the fraction of light which has not been scattered and reflected by the wash liquor or dirt, being received by the receiver 3, a phototransistor.

The transmitter 3 is controlled by the control and evaluation circuit 11 by means of the circuit 5 and with the aid of a pulse-width modulated (PWM) signal, in order to control the illumination level. The receiver 4 drives a photocurrent that is dependent on the received illumination level. The anti-aliasing filter 10, which is used to convert the pulsed photocurrent into a direct voltage signal, generates a voltage $U_a$ which is then evaluated by the control and evaluation circuit 11. This evaluates the voltage $U_a$ and then comes to a turbidity decision. Using this information it is possible to individually adapt a wash program to the actual conditions.

The advantage in using a turbidity sensor lies in being able to individually adjust wash programs to the actual state of the wash liquor. Based on the information from the sensor device a decision may be made as to whether it is necessary to replace the wash liquor. The volume of water in a rinse cycle can be considerably reduced hereby. Water is replaced only if this is actually necessary.

FIG. 3 shows a family of curves which illustrates the connection between the pulse/pause ratio PWM (pulse-duty factor) and the voltage $U_{AD}$ (=$U_a$) as a function of different turbidities. Each of the measured curves MK1 ..., MK8 has a linear region and a saturation region. The gradient in the linear region becomes smaller as the turbidity of the measured wash liquor increases. Measured curve MK1 illustrates the characteristic in the case of clear wash liquid. FIG. 3 shows the calibration window 100, already described in the introduction, which lies in the saturation region of measured curve MK1. As already described, this conventionally results firstly in high measuring uncertainty in the reference measured value measuring procedure. The figure shows an example in which a measuring uncertainty of approx. 30 digits (cf. reference character 105) is illustrated. Secondly, the measurement of further turbidities is carried out with low pulse-duty factors (between 60 and 90 digits, cf. reference characters 101, 102), whereby only low measurement dynamics are used. Using the measured curve MK8 (severe turbidity) it can easily be seen that the measuring accuracy and the resolution of the sensor device are better with an optimally high pulse-duty factor, however. Whereas a resolution of 20 digits is produced with a pulse-duty factor of 90 digits, for example, the resolution is 60 digits already with a pulse-duty factor of 230 digits.

Owing to the linear connection between the pulse-duty factor and the measured value ($U_{AD}$), an evaluation of the turbidity can be made on the basis of a turbidity gradient in order to be able to fully utilize the advantages such as the increase in measurement dynamics.

Figure 6:
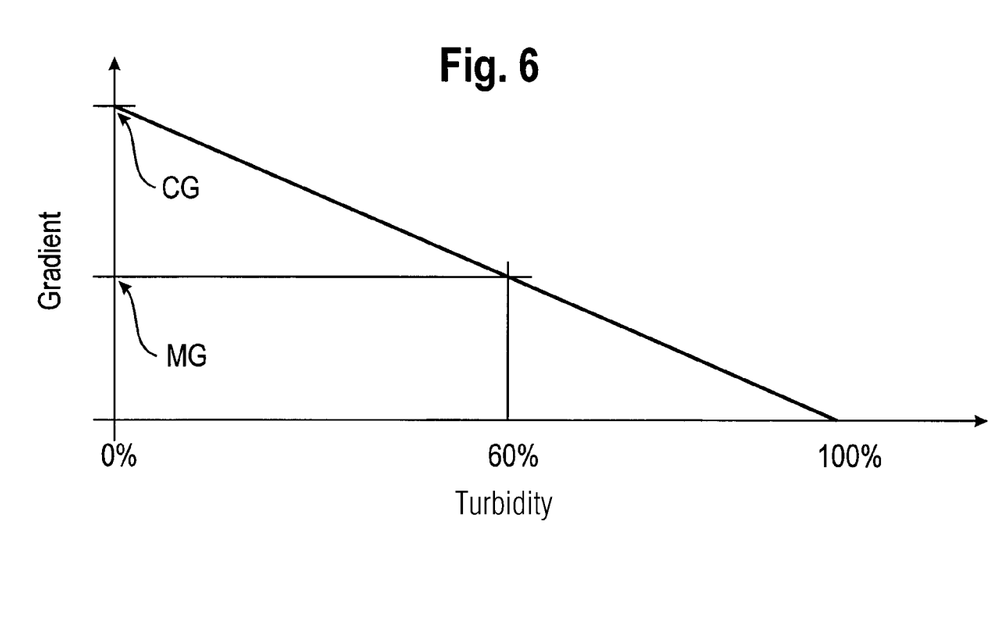
FIG. 6 shows a graph from which the connection between the gradient of turbidity and the turbidity of the wash liquor to be measured can be seen.

FIG. 6 shows the connection between the gradient of the turbidity (gradient) and the turbidity. This connection is linear, i.e. the turbidity gradient decreases linearly as the turbidity increases. The intersection point of the curve with the horizontal axis is at 100% turbidity. This intersection point is identical for all turbidity sensors. The gradient at 0% turbidity (calibration gradient CG) can vary in different turbidity sensors, for example owing to manufacturing tolerances in the semiconductor components. The intersection point of the curve with the y axis is therefore determined by the quality of the turbidity sensor. The curve which connects the intersection points of the respective axes together is always linear, however.

The procedure for determining an absolute level of turbidity of a wash liquor to be measured therefore consists in firstly determining a calibration gradient CG at 0% turbidity of the wash liquor and then determining a measured gradient MG in the following rinse cycle. The level of turbidity turb of the wash liquor can be determined from these two values according to the formula $$turb = \left(1 - \frac{MG}{CG}\right) * 100\% \qquad \text{(Equation 1)}$$

Figure 4:
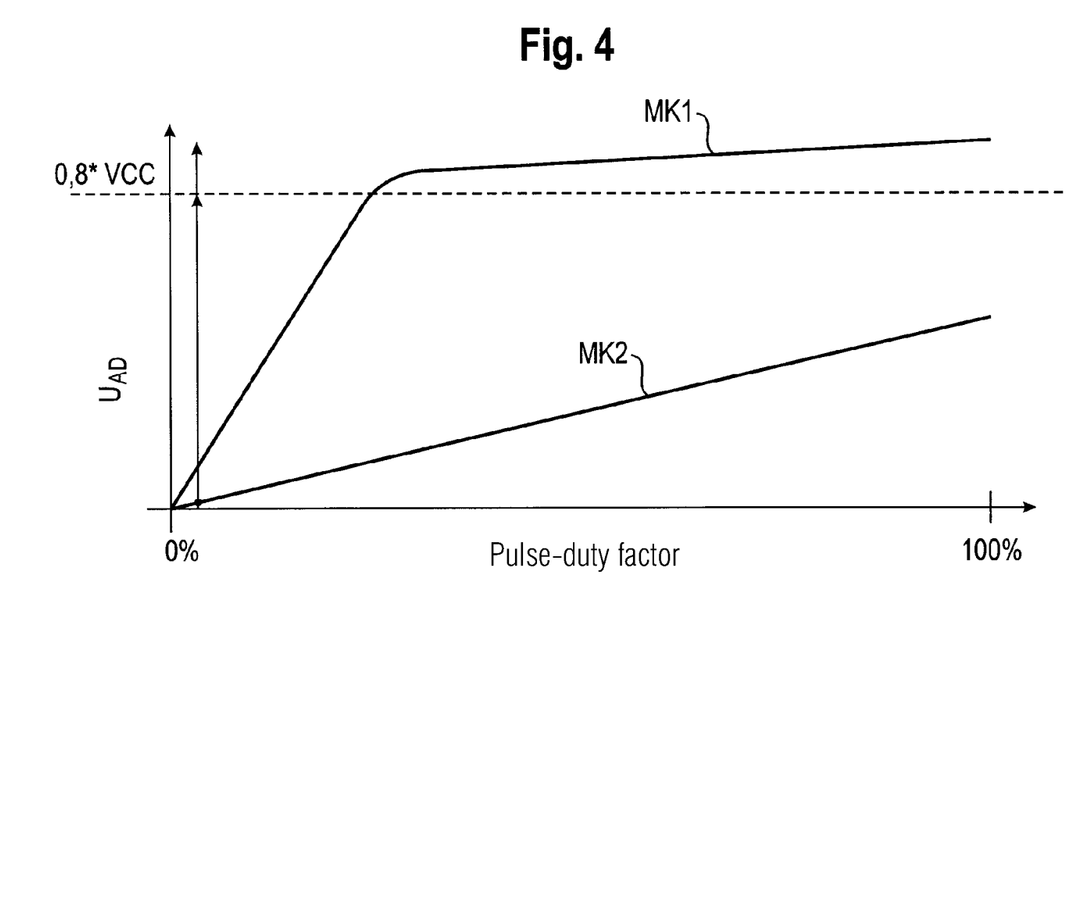
FIG. 4 shows a graph illustrating the connection between A/D converted voltage at the input of the control and evaluation device and pulse-duty factor.

The gradient between the pulse-duty factor and the voltage $U_a = U_{AD}$ supplied to the evaluation device 11 is also proportional to the turbidity. FIG. 4 shows the measured curves which are used to determine the calibration gradient CG and the measured gradient MG. Measured curve MK1 shows the characteristic at 0% turbidity; measured curve MK2 the characteristic in the case of turbid wash liquor. The gradient is in each case determined only in a linear region of the measured curves. A limiting value is shown in the figure and this lies at 80% of the supply voltage Vcc of the transmitter 3 (cf. FIG. 1). If the voltage value $U_a$ exceeds the limiting value during a measuring process, in which the pulse-duty factor is increased in increments, starting from 0, increasing of the pulse-duty factor is terminated and the gradient determined using the previous measured values. As may clearly be seen from FIG. 4, it is possible to completely utilize the pulse-duty factor up to 100% as turbidity increases, i.e. at a lower gradient.

Figure 5:
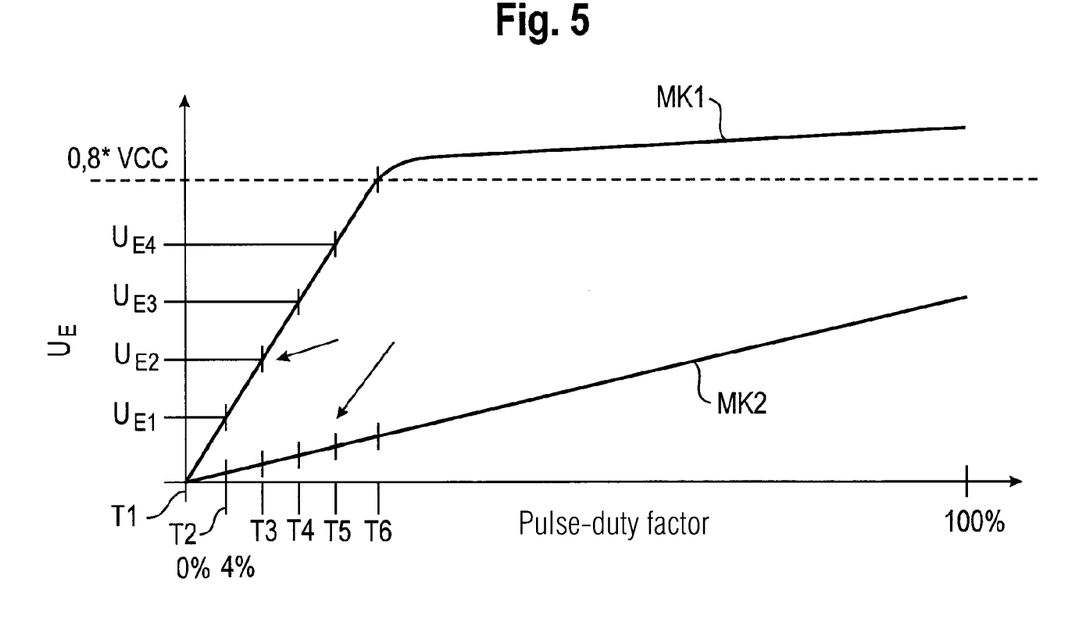
FIG. 5 shows the graph known from FIG. 4, with the aid of which determination of the gradient of a certain turbidity can be seen.

The procedure for determining the gradient will be described with reference to FIG. 5. In this exemplary embodiment the increment for increasing the pulse-duty factor is fixed by way of example at 4%. A total of six pulse-duty factors T1, ..., T6 are plotted along the x axis, at which factors the voltage value is multiply measured in each case. Multiple measurement at each of the pulse-duty factors T1, ..., T6 is subjected to averaging, the result of averaging ($U_{E1}$, $U_{E2}$, $U_{E3}$, $U_{E4}$) being used to determine the gradient CG or MG. To determine the gradients CG and MG the total of the measured values $U_{E1}$, $U_{E2}$, ... is compared with the total of the pulse-duty factors T1, T2, ... Once the gradients CG and MG are determined the absolute level of turbidity can be determined by equation 1.

The inventive sensor device has the advantage that an absolute level of turbidity can be determined which is highly accurate. A particularly good adjustment of a wash program, for example in a dishwasher, is possible as a result, whereby the dishwasher can be operated so as to be particularly sparing with resources.

| List of reference characters | |
|---|---|
| 1 | sensor device |
| 2 | turbidity sensor |
| 3 | transmitter |
| 4 | receiver |
| 5 | circuit |
| 6 | resistor |
| 7 | transistor |
| 8 | resistor |
| 9 | resistor |
| 10 | anti-aliasing filter |
| 11 | control and evaluation device |
| 12 | output |
| 13 | input |
| 14 | resistor |
| 15 | charge-coupled accumulator |
| 16 | resistor |
| 17 | charge-coupled accumulator |
| 100 | calibration window |
| 101 | PWM value 1 |
| 102 | PWM value 2 |
| 103 | voltage |
| 104 | voltage |
| 105 | voltage difference |
| 106 | limit voltage |
| CG | calibration gradient |
| MG | measured gradient |
| MK1 | measured curve (clear liquid) |
| MK2 | measured curve (turbid liquid) |
| MK3 | measured curve (turbid liquid) |
| MK4 | measured curve (turbid liquid) |
| MK5 | measured curve (turbid liquid) |
| MK6 | measured curve (turbid liquid) |
| MK7 | measured curve (turbid liquid) |
| MK8 | measured curve (turbid liquid) |
| PWM | pulse-dutyfactor |
| U | voltage |
| $U_{E1}$ | voltage |
| $U_{E2}$ | voltage |
| $U_{E3}$ | voltage |
| $U_{E4}$ | voltage |
| 4 | pulse-duty factor |
| T2 | pulse-duty factor |
| T3 | pulse-duty factor |
| T4 | pulse-duty factor |
| T5 | pulse-duty factor |
| T6 | pulse-duty factor |

The invention claimed is:

1. A sensor device for detecting a turbidity of wash liquor, comprising:
   an optical transmitter including an LED for producing illumination responsive to a control signal;
   an optical receiver including a phototransistor for producing an output voltage responsive to illumination received from the transmitter, wherein the wash liquor to be tested flows between the optical transmitter and the optical receiver; and
   an electronic control and evaluation circuit for controlling the optical transmitter and receiving the output voltage from the optical receiver to (a) carry out a reference measurement by means of the optical transmitter and the optical receiver to determine a turbidity gradient by determining a change in output voltage of the receiver as a linear function of the luminosity emitted by the transmitter in order to determine a reference measured value of a turbidity gradient of a reference liquid;
   (b) carry out a turbidity measurement on the wash liquor to be measured by means of the optical transmitter and the optical receiver to determine a turbidity gradient by determining a change in output voltage of the receiver as a linear function of the luminosity emitted by the transmitter in order to determine a test measured value of the turbidity gradient of wash liquor;
   (c) relate the reference measured value to the test measured value as a function of the optical transmitter control signal and the voltage output from the optical receiver by calculating the ratio of reference turbidity to wash liquor turbidity; and
   (d) determine a characteristic value as a percentage of absolute level of turbidity for a determined turbidity of the wash liquor therefrom and transmit the characteristic value as a measurement signal.

2. The sensor device of claim 1, wherein the sensor device is installed in a domestic dishwasher.

3. The sensor device of claim 1,
   wherein the optical transmitter is structured to emit an illumination level;
   wherein the control and evaluation circuit is structured to adjust the illumination level using a pulse-width modulated signal;
   wherein the optical receiver is structured to receive the illumination level and, as a function of the received illumination level, to supply the control and evaluation device with a voltage value for determining the characteristic value characterizing the turbidity; and
   wherein the control and evaluation circuit is structured to adjust a plurality of pulse-width modulated signals with different pulse-duty factors for determining the gradient of the turbidity; to detect respective voltage values resulting from the different pulse-duty factors; and to determine the gradient of the turbidity from a plurality of detected pairs of values.

4. The sensor device of claim 3, wherein the control and evaluation circuit is structured to carry out a plurality of measurements for each of the different pulse-duty factors, in which one voltage value respectively is determined; and wherein, after averaging all measured voltage values, the characteristic value characterizing the turbidity is determined and taken into account for further processing.

5. The sensor device of claim 3, wherein the control and evaluation circuit is structured to perform a test as to whether the characteristic value characterizing the turbidity is in a linear working area of the sensor device.

6. The sensor device of claim 3, wherein the control and evaluation circuit is structured to determine the gradient if a predefined condition is met.

7. The sensor device of claim 6, wherein the predefined condition is a predefined voltage value.

8. The sensor device of claim 3, wherein, for determining the gradient with the control and evaluation circuit, a step size of a pulse-duty factor is incremented in a linear region, and wherein the increment is adjusted as a function of a predetermined measuring accuracy.

9. The sensor device of claim 3, wherein, for determining the gradient, a total of measured values is compared with a total of measured pulse-duty factors.

10. The sensor device of claim 1, wherein the characteristic value is calculated in accordance with:

$$turb = \left(1 - \frac{MG}{CG}\right) * 100\%$$

where turb is the turbidity,
MG is a measured gradient, and
CG is a calibration gradient.

11. The sensor device of claim 1, wherein the reference measured value is determined one of without the wash liquor and with clear wash liquor.

12. The sensor device of claim 1, wherein the test measured value is determined in a rinse cycle that follows the reference measurement.

13. The sensor device of claim 1, characterized in that the optical transmitter and the optical receiver operate on infrared basis.

14. A method for detecting a turbidity of wash liquor that flows between a transmitter and a receiver, the method comprising:
producing illumination responsive to a control signal using the transmitter;
producing an output voltage using the receiver, the output voltage being responsive to illumination received from the transmitter, and
controlling the optical transmitter and receiving the output voltage from the optical receiver using an electronic control and evaluation circuit; and
using the control and evaluation circuit to perform the steps of:
carrying out a reference measurement to determine a turbidity gradient by determining a change in output voltage of the receiver as a linear function of the luminosity emitted by the transmitter in order to determine a reference measured value of a turbidity gradient of a reference liquid;
carrying out a turbidity measurement on the wash liquor to be measured to determine a turbidity gradient by determining a change in output voltage of the receiver as a linear function of the luminosity emitted by the transmitter in order to determine a test measured value of the turbidity gradient of wash liquor;
relating the reference measured value to the test measured value as a function of the optical transmitter control signal and the voltage output from the optical receiver by calculating the ratio of reference turbidity to wash liquor turbidity;
determining a characteristic value as a percentage of absolute level of turbidity for a determined turbidity of the wash liquor therefrom;
transmitting the characteristic value as a measurement signal.

15. The method of claim 14, wherein the turbidity of the wash liquor is detected in a domestic dishwasher.

16. The method as claimed in claim 14, further comprising:
emitting an illumination level by the transmitter;
adjusting the illumination level by the control and evaluation circuit using a pulse-width modulated signal;
receiving the illumination level by the receiver;
supplying, as a function of the received illumination level, a voltage level from the receiver to the control and evaluation circuit so as to determine the characteristic value characterizing the turbidity;
adjusting a plurality of pulse-width modulated signals with different pulse-duty factors by the control and evaluation circuit so as to determine the gradient;
detecting respective voltage values resulting from the different pulse-duty factors by the control and evaluation circuit; and
determining the gradient of the turbidity from a plurality of detected pairs of values by the control and evaluation circuit.

17. The method of claim 14, wherein the control and evaluation circuit carries out a plurality of measurements for each of the different pulse-duty factors, in which one voltage value respectively is determined; and wherein, after averaging all measured voltage values, the characteristic value characterizing the turbidity is determined and taken into account for further processing.

18. The method of claim 14, wherein the control and evaluation circuit tests whether a measured value is in a linear working area of the sensor device.

19. The method of claim 16, wherein determination of the gradient is carried out if a measured value meets a predefined condition.

20. The method of claim 19, wherein the predefined condition is a predefined voltage value.

21. The method of claim 16, wherein, for determining the gradient with the control and evaluation circuit, a step size of the pulse-duty factor is incremented in a linear region, and wherein the increment is adjusted as a function of a predetermined measuring accuracy.

22. The method of claim 16, wherein, for determining the gradient, a total of measured values is compared with a total of measured pulse-duty factors.

23. The method of claim 16, wherein the characteristic value is calculated in accordance with:

$$turb = \left(1 - \frac{MG}{CG}\right) * 100\%$$

where turb is the turbidity,
MG is a measured gradient, and
CG is a calibration gradient.

24. The method of claim 14, wherein the reference measured value is determined one of without the wash liquor and with clear wash liquor.

25. The method of claim 14, wherein the test measured value is determined in a rinse cycle that follows the reference measurement.

26. A sensor device for detecting a turbidity of wash liquor, comprising:
an optical transmitter structured to emit an illumination level;
an optical receiver structured to receive the illumination level, wherein the wash liquor to be tested flows between the optical transmitter and the optical receiver; and
an electronic control and evaluation circuit structured to adjust the illumination level using a pulse-width modulated signal; to adjust a plurality of pulse-width modulated signals with different pulse-duty factors for determining the gradient of the turbidity; to detect respective voltage values resulting from the different pulse-duty factors; and to determine the gradient of the turbidity from a plurality of detected pair of values, wherein the optical receiver supplies the control and evaluation circuit with a voltage value based on the received illumination level for determining a characteristic value characterizing the turbidity.

27. A method for detecting a turbidity of wash liquor that flows between a transmitter and a receiver comprising the steps of:
    emitting an illumination level by the transmitter;
    adjusting the illumination level by a control-and-evaluation circuit using a pulse-width modulated signal;
    receiving the illumination level by the receiver;
    supplying, as a function of the received illumination level, a voltage level from the receiver to the control and evaluation device so as to determine a characteristic value characterizing the turbidity;
    adjusting a plurality of pulse-width modulated signals with different pulse-duty factors by the control and evaluation circuit so as to determine a turbidity gradient;
    detecting respective voltage values resulting from the different pulse-duty factors by the control and evaluation circuit; and
    determining the gradient of the turbidity from a plurality of detected pairs of values by the control-and-evaluation circuit.

* * * * *

UNITED STATES PATENT AND TRADEMARK OFFICE
CERTIFICATE OF CORRECTION

PATENT NO.      : 8,441,646 B2
APPLICATION NO. : 12/667697
DATED           : May 14, 2013
INVENTOR(S)     : Fauth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 605 days.

Signed and Sealed this
Eighth Day of September, 2015

Michelle K. Lee
*Director of the United States Patent and Trademark Office*